United States Patent
Klatt et al.

(10) Patent No.: US 6,620,964 B2
(45) Date of Patent: Sep. 16, 2003

(54) PREPARATION OF DIHYDROXYCARBOXYLIC ESTERS IN THE ABSENCE OF SOLVENTS

(75) Inventors: Martin Jochen Klatt, Bad Dürkheim (DE); Markus Niebel, Mannheim (DE); Melanie Erhardt, Lambsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/307,333

(22) Filed: Dec. 2, 2002

(65) Prior Publication Data

US 2003/0109720 A1 Jun. 12, 2003

(30) Foreign Application Priority Data

Dec. 7, 2001 (DE) .......................................... 101 60 149

(51) Int. Cl.$^7$ ................................................ C07C 69/66
(52) U.S. Cl. ....................... 560/186; 560/145; 560/180; 549/39
(58) Field of Search ................................. 560/186, 145, 560/180; 549/39

(56) References Cited

U.S. PATENT DOCUMENTS 5,530,143 A * 6/1996 Balkenhohl et al. .......... 549/39
6,013,833 A    1/2000 Gewald et al. ............. 560/145

FOREIGN PATENT DOCUMENTS

EP    487 986    6/1992
EP    863 125    9/1998

OTHER PUBLICATIONS

Bringmann et al. "A Short and Productive Synthesis of (R)–α–Lipoic Acid" Verlag der Zeitschrift für Naturforschung Tubingen (1999) pp. 655–661.

* cited by examiner

Primary Examiner—Alan L. Rotman
Assistant Examiner—Hector Reyes
(74) Attorney, Agent, or Firm—Keil & Weinkauf

(57) ABSTRACT

A description is given of a process for preparing dihydroxycarboxylic esters and of an overall process for preparing R-(+)-α-lipoic acid.

6 Claims, No Drawings

PREPARATION OF DIHYDROXYCARBOXYLIC ESTERS IN THE ABSENCE OF SOLVENTS

The present invention relates to a process for preparing dihydroxycarboxylic esters and an overall process for preparing R-(+)-α-lipoic acid.

Dihydroxycarboxylic esters are valuable intermediates and synthesis building blocks in organic chemistry. In particular, (6S)-6,8-dihydroxyoctanoic esters serve as intermediates for the synthesis of enantiomerically pure R-(+)-α-lipoic acid.

EP 487 986 discloses preparing (6S)-6,8-dihydroxyoctanoic esters by reducing the corresponding (3S)-3-hydroxyoctanedioic diesters with complex hydrides in the presence of aprotic solvents.

Using this process, the yields which are good but are still in need of improvement are achieved. In addition, the process has the disadvantages that solvents and relatively large amounts of complex hydrides must be used.

It is an object of the present invention, therefore, to provide a process for preparing dihydroxycarboxylic esters which does not have the disadvantages of the prior art and provides the dihydroxycarboxylic esters without solvent and in improved yields.

We have found that this object is achieved by a process for preparing dihydroxycarboxylic esters of the formula I,

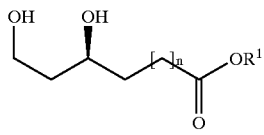

where
n is 1, 2, 3, 4, 5, 6 or 7 and
$R^1$ is an unsubstituted or substituted $C_1$–$C_{20}$-alkyl, $C_2$–$C_{20}$-alkenyl, $C_2$–$C_{20}$-alkynyl, $C_3$–$C_8$-cycloalkyl, aralkyl, aryl, hetarylalkyl or hetaryl radical,
which comprises reacting hydroxycarboxylic diesters of the formula II,

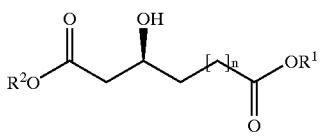

where
$R^2$ is a radical $R^1$ independent of $R^1$,
with complex hydrides in the absence of a solvent.

The index n which is the number of —CH$_2$— radicals is 1, 2, 3, 4, 5, 6 or 7, preferably 3. In a preferred embodiment of the process, therefore dihydroxyoctanoic esters are prepared according to the invention.

The radicals $R^1$ and $R^2$ can be different or identical. The radicals $R^1$ and $R^2$ are therefore independently of one another an unsubstituted or substituted $C_1$–$C_{20}$-alkyl, preferably $C_1$–$C_{12}$-alkyl, particularly preferably $C_1$–$C_4$-alkyl, an unsubstituted or substituted $C_2$–$C_{20}$-alkenyl, preferably $C_2$–$C_{12}$-alkenyl, particularly preferably $C_1$–$C_4$-alkenyl, an unsubstituted or substituted $C_2$–$C_{20}$-alkynyl, preferably $C_2$–$C_{12}$-alkynyl, particularly preferably $C_1$–$C_4$-alkynyl, an unsubstituted or substituted $C_3$–$C_8$-cycloalkyl, an unsubstituted or substituted aralkyl, an unsubstituted or substituted aryl, an unsubstituted or substituted hydroxyalkyl or an unsubstituted or substituted hetaryl.

For all substituted radicals of the present invention, if the substituents are not specified in more detail, independently of one another there may be up to five substituents, for example selected from the following group:
halogen, in particular F or Cl, unsubstituted or substituted $C_1$–$C_{12}$-alkyl, in particular $C_1$–$C_4$-alkyl, for example methyl, $CF_3$, $C_2F_5$ or $CH_2F$ or $C_1$–$C_{12}$-alkoxy, in particular $C_1$–$C_4$-alkoxy.

$C_1$–$C_{12}$-Alkyl radicals for $R^1$ and $R^2$ are independently of one another, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, heptyl, octyl, nonyl, decyl, undecyl or dodecyl, preferably branched or unbranched $C_1$–$C_4$-alkyl radicals, for example methyl, ethyl, propyl, 1-methylethyl, butyl, 1-methylpropyl, 2-methylpropyl or 1,1-dimethylethyl, particularly preferably methyl.

A $C_2$–$C_{12}$-alkenyl radical for $R^1$ and $R^2$ is, independently of one another, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 15 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-l-methyl-2-propenyl, 1-ethyl-2-methyl-2-propenyl and the corresponding heptenyls, octenyls, nonenyls, decenyls, undecenyls and dodecenyls.

A $C_2$–$C_{12}$-alkynyl radical for $R^1$ and $R^2$ is, independently of one another, for example, ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-l-methyl-2-propynyl, preferably ethynyl, 2-propynyl, 2-butynyl, 1-methyl-2-propynyl or 1-methyl-2-butynyl, and the corresponding heptynyls, octynyls, nonynyls, decynyls, undecynyls and dodecynyls.

A $C_3$–$C_8$-cycloalkyl radical for $R^1$ and $R^2$ is, independently of one another, for example, cyclopropyl, cyclobutyl, cyclopentyl, cyclohexyl, cycloheptyl or cyclooctyl.

Preferred unsubstituted or substituted aryl radicals for $R_1$ and $R_2$ are, independently of one another, unsubstituted or substituted phenyl, 1-naphthyl or 2-naphthyl.

Preferred unsubstituted or substituted arylalkyl radicals for $R_1$ and $R_2$ are, independently of one another, unsubstituted or substituted benzyl or ethylenephenyl (homobenzyl).

Hetaryl radicals for $R^1$ and $R^2$ are, independently of one another, for example radicals such as 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl.

Substituted hetaryl radicals $R^1$ and $R^2$ are, independently of one another, also anellated derivatives of the abovementioned hetaryl radicals, for example indazole, indole, benzothiophene, benzofuran, indoline, benzimidazole, benzthiazole, benzoxazole, quinoline, 2,3-dihydro-1-benzofuran, furo[2,3]pyridine, furo[3,2]pyridine or isoquinoline.

Hetarylalkyl radicals for $R^1$ and $R^2$ are, independently of one another, radicals which are composed, for example, of $C_1$–$C_6$-alkylene radicals and of the above-described hetaryl radicals, for example the radicals —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, $CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, —$CH_2$—$CH_2$-2-thiazolyl, —$CH_2$—$CH_2$-4-thiazolyl, or —$CH_2$—$CH_2$-5-thiazolyl.

Preferred radicals for $R^1$ and $R^2$ are, independently of one another, unsubstituted radicals. Particularly preferred radicals for $R^1$ and $R^2$ are, independently of one another, the above-described $C_1$–$C_{12}$-alkyl radicals, in particular $C_1$–$C_4$-alkyl, in particular methyl.

In a particularly preferred embodiment, the radicals $R^1$ and $R^2$ are identical.

The starting compounds of the inventive process are the hydroxycarboxylic diesters of the formula II. Preparation of these starting compounds is known per se and is described, for example, in EP 487 986 and in the references cited therein. Preferred hydroxycarboxylic diesters of the formula II as starting compounds are composed of the above-described preferred radicals $R^1$ and $R^2$ and the preferred index n.

Particularly preferred hydroxycarboxylic diesters of the formula II as starting compound are:

dimethyl (3S)-3-hydroxyoctanedioate, 1-ethyl 8-methyl (3S)-3-hydroxyoctanedioate, 8-methyl 1-propyl (3S)-3-hydroxyoctanedioate, 8-methyl 1-isopropyl (3S)-3-hydroxyoctanedioate, 1-butyl 8-methyl (3S)-3-hydroxyoctanedioate, 1-sec-butyl 8-methyl (3S)-3-hydroxyoctanedioate, 8-methyl 1-tert-butyl (3S)-3-hydroxyoctanedioate, 8-methyl 1-octyl (3S)-3-hydroxyoctanedioate, 8-methyl 1-phenyl (3S)-3-hydroxyoctanedioate and 1-(2-ethylhexyl) 8-methyl(3S)-3-hydroxyoctanedioate.

A particularly preferred starting compound is dimethyl (3S)-3-hydroxyoctanedioate.

Dihydroxycarboxylic esters of the formula I are prepared inventively as product compounds by reacting hydroxycarboxylic diesters of the formula II as starting compounds with complex hydrides and thus by reducing the hydroxycarboxylic diesters of the formula II as starting compounds in the absence of a solvent.

"In the absence of a solvent" according to the invention means that during the inventive reaction no solvent is present. Solvents are taken to meaning, in a manner known per se, inert liquid compounds which do not participate in the reaction as reactants and which can dissolve or suspend the compounds of the reaction mixture.

In particular, solvents are aprotic solvents, for example aliphatic and aromatic hydrocarbons, for example hexane, cyclohexane, toluene, benzene and xylene, and ethers, for example dioxane, diethyl ether and tetrahydrofuran.

The hydroxycarboxylic diesters of the formula II, the complex hydrides or the alcohols released during the reaction are not considered to be solvents.

After the reaction and during the workup, it is advantageous to use solvents in order to remove byproducts and to isolate the desired products.

The inventive process can be carried out in principle in all reactors which ensure sufficient mixing of the reaction mixture during the reaction.

Particularly preferred reactors for the inventive process are kneading apparatuses which, as is known, can also be called kneaders.

The inventive process can be carried out batchwise or continuously.

In a preferred embodiment, the procedure of the inventive process is carried out batchwise.

For the batchwise embodiment of the process, the use of batchwise kneading apparatuses as reactors, for example the use of single-arm kneaders, blade kneaders, planetary kneaders or rotary mixers, is particularly preferred.

In a further preferred embodiment, the inventive process is carried out continuously.

Preferably, the continuous process is carried out in such a manner that the hydroxycarboxylic diesters of the formula II and the complex hydrides are fed continuously to a reactor and the dihydroxycarboxylic esters of the formula I are removed continuously from the reactor.

For the continuous embodiment of the process, the use of continuous kneading apparatuses as reactors is preferred. Preferred continuous kneading apparatuses are extruders, roller kneaders, for example single and multiple roll systems and roller mills and also screw kneaders, for example single-screw kneaders with and without axial screw movements and multiple screw kneaders. Particularly preferred continuous kneading apparatuses are extruders and screw kneaders.

Preferred complex hydrides are borohydrides, in particular ammonium borohydride, lithium borohydride, potassium borohydride and sodium borohydride, and also alkyl- and alkoxy-substituted borohydrides, for example lithium triethylborohydride and sodium trimethoxyborohydride. A particularly preferred complex hydride in the inventive process is sodium borohydride.

The molar ratio of complex hydrides to the hydroxycarboxylic diester of the formula II is not critical and is typically from 0.5:1 to 3:1, preferably from 0.5:1 to 1:1, particularly preferably from 0.6:1 to 0.8:1.

The temperature at which the inventive process is carried out is not critical and is typically from 0 to 150° C., preferably from 10 to 60° C. The inventive process is typically carried out at atmospheric pressure, but can also be carried out at reduced or slightly elevated pressure, preferably at from 0.1 to 10 bar. The reaction times are not critical and are typically from 0.1 to 5 hours, in particular from 0.5 to 1 hour.

The dihydroxycarboxylic esters of the formula I are isolated in a manner known per se, for example, by working up the reaction mixture by hydrolysis, extraction and drying.

The invention process has the advantage that the dihydroxycarboxylic esters of the formula I can be prepared without the use of solvents, in high yields, rapid reaction times and using smaller amounts of complex hydrides.

The invention further relates to an overall process for preparing R-(+)-α-lipoic acid using the inventive process as an intermediate step.

The invention therefore relates to a process for preparing R-(+)-α-lipoic acid of the formula IV

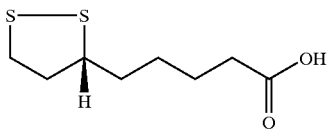

IV which comprises preparing dihydroxycarboxylic esters of the formula I, where n is 3, by reacting the corresponding hydroxycarboxylic diesters of the formula II with complex hydrides in the absence of a solvent and, in a manner known per se, a) converting these dihydroxycarboxylic esters of the formula I in organic solution using a sulfonyl chloride and a tertiary nitrogen base into the bissulfonic esters of I,
b) reacting these bissulfonic esters with sulfur and an alkali metal disulfide in a polar solvent to give the R-α-lipoic ester and
c) converting this ester into the R-(+)-α-lipoic acid of the formula IV.

The example below illustrates the invention.

EXAMPLE 1

45.3 g (0.2 mol) of enantiomerically pure dimethyl (3S)-3-hydroxyoctanedioate were mixed in a Haake kneader at from 30 to 40° C. with 5.2 g of sodium borohydride (0.14 mol, 0.7 equivalents). The reaction mixture was kneaded until the reaction was complete (TLC monitoring, 40 min). The intermediate methyl borate was then taken up in methanol and hydrolyzed under acidic conditions. The desired methyl (6S)-6,8-dihydroxyoctanoate was extracted with ethyl acetate. After drying the organic phase, this was cooled to 0° C., and the product which crystallized out was filtered off. 34.5 g of methyl (6S)-6,8-dihydroxyoctanoate in the form of white crystals were obtained (90% yield).

We claim:

1. A process for preparing dihydroxycarboxylic esters of the formula I,

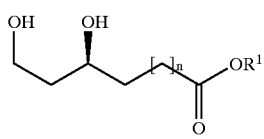

I where
n is 1, 2, 3, 4, 5, 6 or 7 and
$R^1$ is an unsubstituted or substituted $C_1$–$C_{20}$-alkyl, $C_2$–$C_{20}$-alkenyl, $C_2$–$C_{20}$-alkynyl, $C_3$–$C_8$-cycloalkyl, aralkyl, aryl, hetarylalkyl or hetaryl radical,
which comprises reacting hydroxycarboxylic diesters of the formula II,

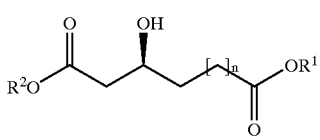

II where
$R^2$ is a radical $R^1$ independent of $R^1$,
with complex hydrides in the absence of a solvent.

2. A process as claimed in claim 1, wherein the reaction is carried out in a kneading apparatus.

3. A process as claimed in claim 1, wherein the reaction is carried out continuously.

4. A process as claimed in claim 3, wherein the hydroxycarboxylic diesters of the formula II and the complex hydrides are fed continuously to a reactor and the dihydroxycarboxylic esters of the formula I are removed continuously from the reactor.

5. A process as claimed in claim 1, wherein the complex hydride used is sodium borohydride.

6. A process for preparing R-(+)-α-lipoic acid of the formula IV

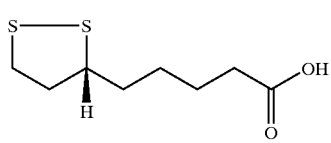

IV which comprises preparing dihydroxycarboxylic esters of the formula I,

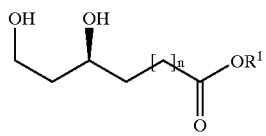

I where
n is 3 and
$R^1$ is an unsubstituted or substituted $C_1$–$C_{20}$-alkyl, $C_2$–$C_{20}$-alkenyl, $C_2$–$C_{20}$-alkynyl, $C_3$–$C_8$-cycloalkyl, aralkyl, aryl, hetarylalkyl or hetaryl radical
by reacting hydroxycarboxylic diesters of the formula II,

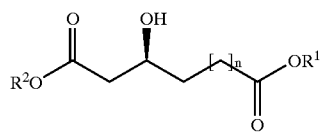

II where
$R^2$ is a radical $R^1$ independent of $R^1$, with complex hydrides in the absence of a solvent and
a) converting these dihydroxycarboxylic esters of the formula I in organic solution using a sulfonyl chloride and a tertiary nitrogen base into the bissulfonic esters of I,
b) reacting these bissulfonic esters with sulfur and an alkali metal disulfide in a polar solvent to give the R-α-lipoic ester and
c) converting this ester into the R-(+)-α-lipoic acid of the formula IV.

* * * * *